(12) United States Patent
Chang et al.

(10) Patent No.: US 10,925,547 B2
(45) Date of Patent: Feb. 23, 2021

(54) SYSTEM FOR MONITORING PHYSIOLOGICAL CONDITION

(71) Applicant: BIONIME CORPORATION, Taichung (TW)

(72) Inventors: Ming-Luen Chang, Taichung (TW); Cheng-Wei Lu, Taichung (TW); Kuo-Chih Ho, Taichung (TW); Kai-Fa Chang, Taichung (TW); Yung-Feng Lai, Taichung (TW); Jui-Chi Weng, Taichung (TW)

(73) Assignee: Bionime Corporation, Taichung (TW)

(*) Notice: Subject to any disclaimer, the term of this patent is extended or adjusted under 35 U.S.C. 154(b) by 459 days.

(21) Appl. No.: 15/866,764

(22) Filed: Jan. 10, 2018

(65) Prior Publication Data
US 2018/0199891 A1    Jul. 19, 2018

(30) Foreign Application Priority Data

Jan. 16, 2017 (TW) .................... 106101352
May 17, 2017 (TW) .................... 106116270
Jun. 30, 2017 (TW) .................... 106122043

(51) Int. Cl.
*A61B 5/00* (2006.01)
*A61B 5/145* (2006.01)
(Continued)

(52) U.S. Cl.
CPC ........ *A61B 5/7275* (2013.01); *A61B 5/14532* (2013.01); *G01N 33/723* (2013.01);
(Continued)

(58) Field of Classification Search
CPC ........ G16H 40/60; G16H 40/67; G16H 50/20; A61B 5/7275; A61B 5/14532; A61B 5/742; G01N 33/723; G01N 33/66
See application file for complete search history.

(56) References Cited

U.S. PATENT DOCUMENTS

2008/0071580 A1* 3/2008 Marcus .................. G06Q 50/24
                                                                                   705/3
2010/0165795 A1* 7/2010 Elder ............... G01N 33/48792
                                                                                  368/10
(Continued)

FOREIGN PATENT DOCUMENTS

WO        2013184896 A1    12/2013

OTHER PUBLICATIONS

Search Report Issued in the European Counterpart Application No. 18151350.8 by the EPO on Jun. 22, 2018.

*Primary Examiner* — Navin Natnithithadha
*Assistant Examiner* — Andrey Shostak
(74) *Attorney, Agent, or Firm* — Rosenberg, Klein & Lee

(57) ABSTRACT

A system for monitoring a physiological condition of a user includes a first measuring apparatus for personal use, a second measuring apparatus for use by medical professionals, and a server. The first measuring apparatus measures a first physiological parameter of the user. The second measuring apparatus measures a second physiological parameter of the user. The server receives the first and second physiological parameters measured by the first and second measuring apparatuses. The measured values of the first and second physiological parameters are associated with a disease condition, a health condition, a nutrient intake condition, a fitness condition or an exercise condition of the user.

20 Claims, 12 Drawing Sheets

(51) Int. Cl.
  *G01N 33/72* (2006.01)
  *G16H 40/67* (2018.01)
  *G16H 50/20* (2018.01)
  G01N 33/66 (2006.01)
  G16H 40/60 (2018.01)

(52) U.S. Cl.
  CPC ............. *G16H 40/67* (2018.01); *G16H 50/20*
      (2018.01); *A61B 5/742* (2013.01); *G01N 33/66*
                  (2013.01); *G16H 40/60* (2018.01)

(56) References Cited

U.S. PATENT DOCUMENTS

| | | | |
|---|---|---|---|
| 2011/0196217 A1* | 8/2011 | Myoujou | A61B 5/14532 600/365 |
| 2012/0094367 A1* | 4/2012 | Sugiyama | G01N 33/723 435/287.1 |
| 2012/0271557 A1* | 10/2012 | Sekimoto | A61B 5/743 702/19 |
| 2013/0277233 A1 | 10/2013 | Blythe et al. | |
| 2014/0273257 A1* | 9/2014 | Batman | A61B 5/14532 436/95 |
| 2014/0324445 A1* | 10/2014 | Carlsgaard | A61B 5/0022 705/2 |
| 2015/0265190 A1* | 9/2015 | Ikebe | A61B 5/681 600/316 |
| 2016/0098539 A1* | 4/2016 | Zamanakos | G16H 10/60 705/3 |
| 2016/0334385 A1* | 11/2016 | Prais | G01N 33/49 |
| 2017/0316176 A1* | 11/2017 | Hasegawa | A61B 5/14546 |

\* cited by examiner

| 2015 Aug | Breakfast | | Lunch | | Dinner | | Bedtime |
|---|---|---|---|---|---|---|---|
| 09 Mon | 245 | | 114 | | 183 | | 138 |
| 08 Sat | 242 | | 157 | 128 | | | 219 |
| 07 | 218 | | 108 | 330 | 127 | | 218 |
| 06 | | | 139 | 195 | | | 207 |
| 05 | 241 | | 120 | | 100 | 190 | |
| 04 | 197 | | 114 | | 147 | 255 | |

—B (after 128)
—R (after 330)

FIG.4

| Measured HbA$_{1c}$ | |
|---|---|
| 2016/4/1 | 6.3% |
| 2016/1/1 | 6.6% |

| Date | Midnight | Waking up | Breakfast | | Lunch | | Dinner | | Bedtime |
|---|---|---|---|---|---|---|---|---|---|
| | | | Before | After | Before | After | Before | After | |
| 32 blood glucose records | | | | | | | | | |
| Est. HbA$_{1c}$ : 5.7% | | | | | | | | | |
| 4/14 Thursday | | | 80 | 102 | 111 | | | | |
| 4/13 Wednesday | | 103 | | | 78 | 130 | 126 | 148 | |
| 4/12 Tuesday | | | 129 | | 89 | 145 | 104 | 121 | |
| 4/11 Monday | | | 130 | | 108 | 173 | 130 | 121 | |
| 4/10 Sunday | | | 107 | | 97 | | 101 | 136 | |
| 4/9 Saturday | | | 138 | | 98 | 196 | 106 | 127 | 84 |
| 4/8 Friday | | | 130 | | 91 | | 100 | | 117 |
| 15 blood glucose records | | | | | | | | | |
| Est. HbA$_{1c}$ : 6.1% | | | | | | | | | |
| 4/7 Thursday | | | 115 | | 111 | | 152 | | 101 |
| 4/6 Wednesday | | | 139 | 164 | 116 | | 94 | 175 | 116 |
| 4/5 Tuesday | | | 139 | | 94 | 178 | 112 | | 134 |
| 4/4 Monday | | | | | | | | | |
| 4/3 Sunday | | | | | | | | | |
| 4/2 Saturday | | | | | | | | | |
| 4/1 Friday | | | | | | | | | |

FIG.6

SYSTEM FOR MONITORING PHYSIOLOGICAL CONDITION

CROSS-REFERENCE TO RELATED APPLICATION

This application claims priority of Taiwanese Patent Application Nos. 106101352, 106116270 and 106122043, respectively filed on Jan. 16, May 17 and Jun. 30, 2017.

FIELD

The disclosure relates to a system for monitoring a physiological condition of a user, and more particularly to a system that integrates data of a first physiological parameter measured by a personal-use measuring apparatus, and data of a second physiological parameter measured by a medical-professional measuring apparatus.

BACKGROUND

In addition to the blood glucose level, the glycated hemoglobin ($HbA_{1c}$) level is also an important index for blood sugar control. Conventional blood glucose meters for self-monitoring of the blood glucose level facilitate self-test of the blood glucose level by a diabetic patient, but these blood glucose meters are usually unable to test the glycated hemoglobin level. For inspection of the glycated hemoglobin level, a professional blood glucose meter, such as a point-of-care testing (POCT) instrument or a biochemical instrument, may be required, resulting in inconvenience for patients who require periodic tracking of the glycated hemoglobin level.

Furthermore, the conventional blood glucose meters lack the functions that facilitate the patients to record and/or observe the variation of the blood glucose levels.

SUMMARY

Therefore, the disclosure is to provide a system that can facilitate periodical tracking of a physiological condition of a user.

According to the disclosure, a system for monitoring a physiological condition of a user includes a first measuring apparatus, a second measuring apparatus and a server. The first measuring apparatus is for personal use, and is configured to measure a first physiological parameter of the user, and to generate a first parameter signal indicating a measured first parameter value of the first physiological parameter measured thereby. The second measuring apparatus is for use by medical professionals, and is configured to measure a second physiological parameter of the user, and to generate a second parameter signal indicating a measured second parameter value of the second physiological parameter measured thereby. The server is communicatively coupled to the first measuring apparatus via a network for receiving the first parameter signal therefrom, and is disposed to receive the second parameter signal via the network. Each of the first and second measured parameter values is associated with a disease condition, a health condition, a nutrient intake condition, a fitness condition or an exercise condition of the user.

According to the disclosure, a system for monitoring a physiological condition of a user includes a first measuring apparatus for personal use, a second measuring apparatus for use by medical professionals, and a server. The first measuring apparatus is configured to measure a blood glucose level of the user, and to generate a first parameter signal indicating a measured blood glucose value of the blood glucose level measured thereby. The second measuring apparatus is configured to measure a glycated hemoglobin level of the user, to generate a second parameter signal indicating a measured glycated hemoglobin value of the glycated hemoglobin level measured thereby, to measure the blood glucose level of the user, and to generate a third parameter signal indicating a measured blood glucose value of the blood glucose level measured thereby. The server is communicatively coupled to the first measuring apparatus via a network for receiving the first parameter signal therefrom, and is disposed to receive the second and third parameter signals via the network, and is configured to calculate an estimated glycated hemoglobin value based on a set of the measured blood glucose values measured by the first measuring apparatus and the second measuring apparatus, and to transmit to at least one application provided by the first server a signal indicating the estimated second parameter value and the measured second parameter value. The at least one application is further configured to compare the estimated second parameter value and the measured second parameter value, and to visually output a notification message when a difference between the estimated second parameter value and the measured second parameter value is greater than a threshold value.

According to the disclosure, a computerized system for visually presenting statistical analysis result of a physiological parameter of a user is proposed to include a storage device, a display device and a computerized device. The storage device stores a set of physiological parameter values measured from the user. The computerized device is communicatively coupled to the storage device and the display device, and is configured to calculate an average and a standard deviation of the physiological parameter values, and to generate a graphical user interface that presents a plot including a horizontal axis to represent event labels corresponding to the physiological parameter values, a vertical axis to represent the average and the standard deviation of the physiological parameter values, an average indicator to indicate a value of the average, and a standard deviation indicator to indicate a value of the standard deviation. At least a portion of the standard deviation indicator is included within the average indicator. The computerized device is further configured to control the display device to visually output the graphical user interface with the plot.

BRIEF DESCRIPTION OF THE DRAWINGS

Other features and advantages of the disclosure will become apparent in the following detailed description of the embodiment (s) with reference to the accompanying drawings, of which:

FIG. 4 shows an exemplary screen where multiple blood glucose values are combined into several pairs;

FIG. 6 is an exemplary table to be displayed by the mobile device and showing measured glycated hemoglobin values, estimated glycated hemoglobin values, and measured blood glucose values classified according to different event labels;

DETAILED DESCRIPTION

Figure 1:
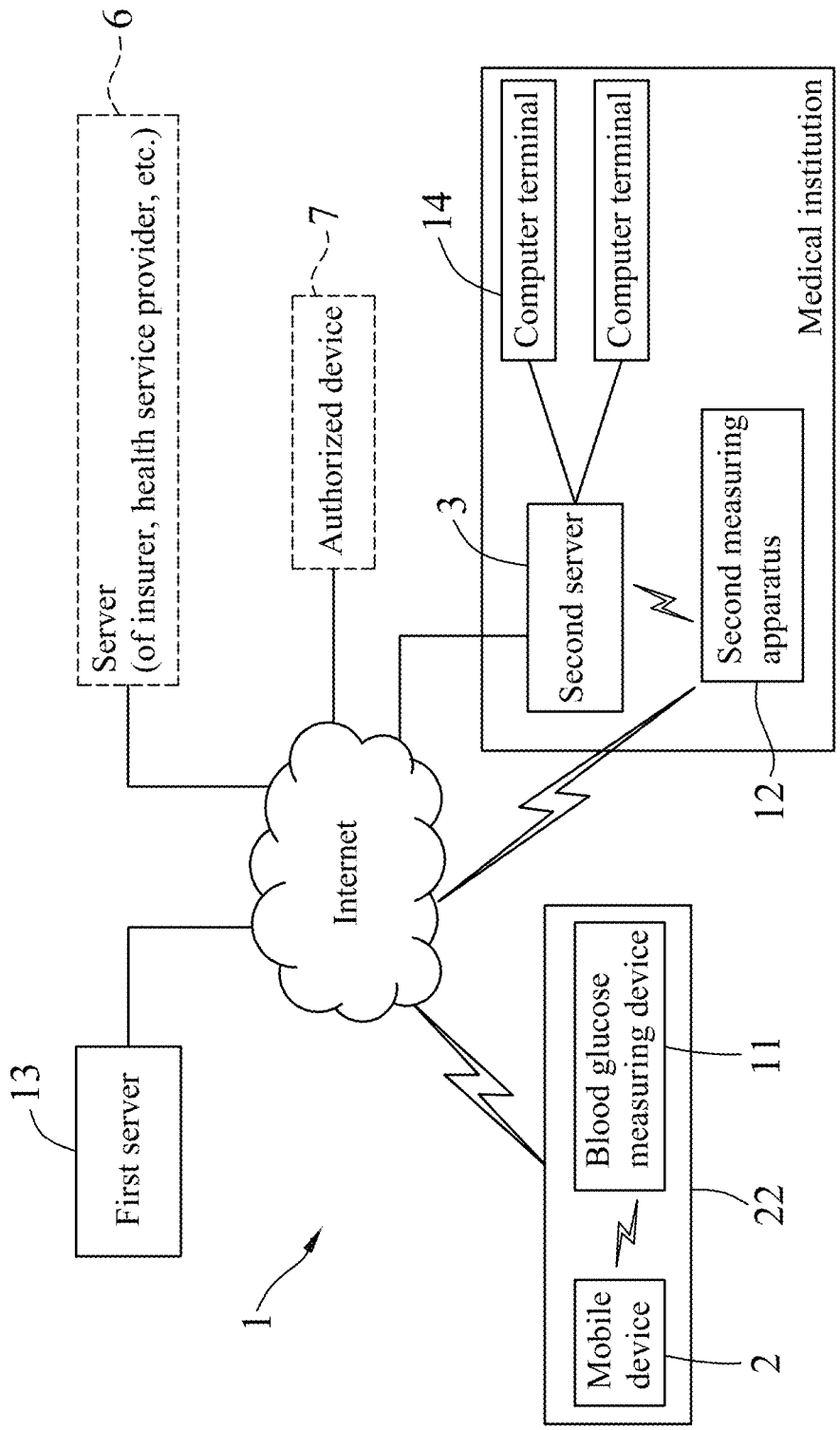
FIG. 1 is a block diagram illustrating an embodiment of the system for monitoring a physiological condition of a user according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, the embodiment of the system 1 for monitoring a physiological condition of a user is shown to include a first measuring apparatus 22 for personal use (e.g., for self-monitoring of the blood glucose level), a first server 13, a second server 3 placed in a medical institution (e.g., a hospital), at least a computer terminal 14 and a second measuring apparatus 12. The computer terminal 14 is connected to the second server 3, and is able to connect to the Internet through the second server 3. In one embodiment, the second server 3 may include a health information system (not shown in FIG. 1) belonging to the medical institution. In one embodiment, the system 1 may optionally include a server of an insurer or a health service provider and/or other authorized devices 7. The first and second measuring apparatuses 22, 12 may be used to monitor physiological parameters, such as blood glucose level and glycated hemoglobin level, which are associated with disease conditions, health conditions, nutrient intake conditions, fitness conditions and/or exercise conditions. The first server 13, the first measuring apparatus 22, the computer terminal 14 and the second measuring apparatus 12 may perform data transmission thereamong via a network, and may execute respective application software to collect and analyze data. The application software may be built in the respective device, downloaded through the network, or implemented as cloud software which can be accessed through a webpage, etc., but this disclosure is not limited to such implementations.

The first measuring apparatus 22 may execute a personal-use first application (not shown) which enables transmission of measured data to the first server 13 for complicated analysis operations, followed by receipt of the analysis operation result. After authorization by the user, the first server 13 may transmit the measured data and/or the analysis operation result to the second server 3, so that the medical professionals may make diagnosis based on the measured data and/or the analysis operation result by use of a professional-use second application (not shown in FIG. 1) provided by the second server 3 via the computer terminal 14. When the measured data generated by the second measuring apparatus 12 is transmitted to the second server 3 for use by the second application and/or to the first server 13, the second server 3 and/or the first server 13 may further transmit the measured data to a mobile device 2 via the Internet for use by the first application. In one implementation, the measured data generated by the first and/or second measuring apparatuses 22, 12 may also be transmitted to and stored in the health information system of the medical institution to serve as medical record(s) of the user. In one implementation, when the medical professionals operate the second application to add/update information related to for example doctor's advises, new patients, new operators, etc., the second server 3 may transmit these newly added or updated information to the second measuring apparatus 12, so that a backend management software (not shown in FIG. 1) of the second measuring apparatus 12 may update settings thereof (e.g., the doctor's advice, the operators, the to-be-measured target) based on the newly added or updated information.

In this embodiment, the first measuring apparatus 22 includes a blood glucose measuring device 11 and the mobile device 2. In one embodiment, the first measuring apparatus 22 may be a single mobile device having a functionality of measuring the blood glucose level (first physiological parameter), which may be built in the mobile device or implemented by an external blood measuring module that is connected to the mobile device via, for example, a USB connection, an audio interface connection, Bluetooth communication, infrared communication, etc. In one implementation, the first measuring apparatus 22 may be a single blood glucose measuring device having a network communication functionality, which may be built in the glucose measuring device or implemented by an external communication module that is coupled to the blood glucose measuring device. However, this disclosure is not limited to the abovementioned implementations.

In this embodiment, the blood glucose measuring device 11 is a blood glucose meter designed for self-monitoring of the blood glucose level. The user may use the blood glucose measuring device 11 to perform self test of the blood glucose level at desired time points, for example, before meal, after meal, after waking up, before bedtime, etc., and to transmit the measured blood glucose value (first parameter value) of the blood glucose level and a data sequence corresponding to the measured blood glucose value to the mobile device 2. The data sequence may include information of, for example, an event label (e.g., a label indicating occasion of measurement with respect to a specific event, such as indicating that the measurement is performed before meal, after meal, after waking up, before bedtime, etc., which may be manually set by the user), a serial number of measurements, measurement time (at which the measured blood glucose value is acquired by the blood glucose measuring device 11), measured date, a time zone (at which the measurement is performed), a model name of the blood glucose measuring device 11, a serial number of the blood glucose measuring device 11, a user account associated with the user, an index indicating whether or not the measured blood glucose value is from a control solution, an index indicating whether or not temperature at which the measurement is performed is out of a predetermined criterion, a data type (e.g., indicating that the measured blood glucose value is generated by the first measuring apparatus 22, by the second measuring apparatus 12, or by manual input), etc. In addition, the data type may be used to determine which medical institution originates the measured blood glucose value when such device is utilized by a medical institution, avoiding possible medical disputes in the future. The mobile device 2 may be a smartphone, a wearable device, a tablet computer, etc., which may receive a manual input of the measured blood glucose value and the corresponding data by the user. The first application may permit further modification or deletion of the manually inputted blood glucose value since the measured blood glucose value may be incorrectly inputted due to misoperation.

Figure 2:
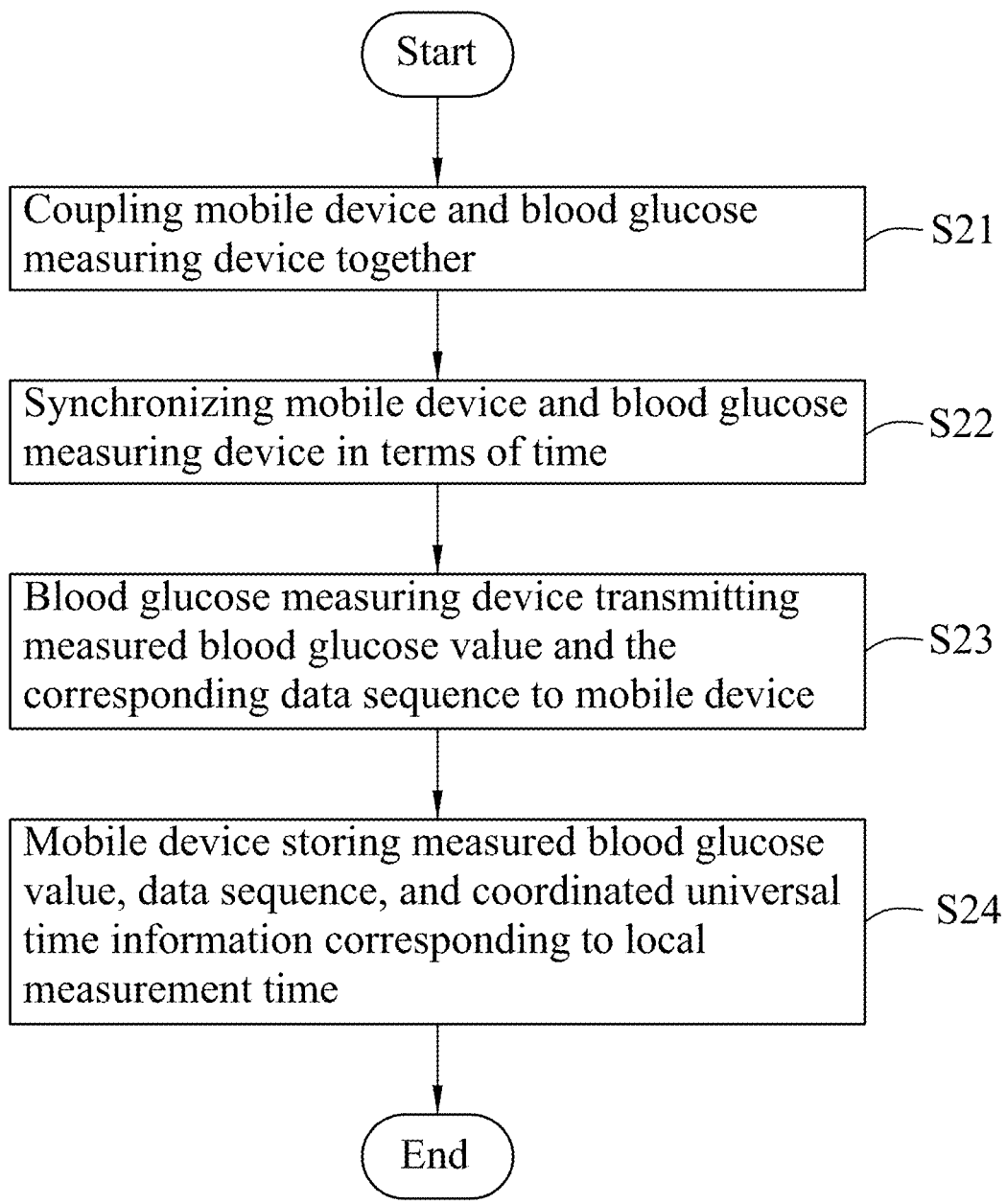
FIG. 2 is a flow chart illustrating steps of synchronization between a mobile device and a blood glucose measuring device of the embodiment in terms of time and data transmission therebetween.

In practice, when the blood glucose measurements are performed at various locations corresponding to different time zones for some reasons (e.g., leisure trips, business trips, etc.), the measurement time information recorded by the blood glucose measuring apparatus 11 may become confusing due to the time difference between the different time zones. In this embodiment, as shown in FIG. 2, after the blood glucose measuring device 11 and the mobile device 2 are communicatively coupled together via wireless or wired connection (step S21), the mobile device 2 transmits local time information of the mobile device 2 to the blood glucose measuring device 11 for synchronization of the two devices in terms of time (step S22). Accordingly, the user may not need to manually adjust the time setting of the blood glucose measuring apparatus 11 when travelling between different time zones. However, if the measured blood glucose values are displayed in sequence according to the measurement time recorded based on local time of the blood glucose measuring device 11, the order of display may not reflect the actual order of measurement when the measurements involve different time zones. To solve this issue, in this embodiment, the blood glucose measuring device 11 transmits a measurement signal indicating the measured blood glucose value and the corresponding data sequence to the mobile device 2 via the first application (step S23), where the measurement time information included in the data sequence is local time information for use in pairing of two measured blood glucose values according to different events, such as dining, exercising, medication intake, etc., while will be made clear in later paragraphs, and the mobile device 2 then stores therein, in response to receipt of the measurement signal, a measurement data piece including the measured blood glucose value, the data sequence, and coordinated universal time information converted thereby from the local measurement time included in the data sequence (step S24). Accordingly, when the mobile device 2 stores two or more measurement data pieces each corresponding to a respective local measurement time point, the mobile device 2 may correctly arrange the measured blood glucose values of the measurement data pieces in chronological order based on the coordinated universal time of the measurement data pieces, and selectively display, via the first application, the measured blood glucose values accordingly in the correct order of measurement. The abovementioned order arrangement operations based on the UTC information may also be applied to the second server 3 via the second application.

Figure 3:
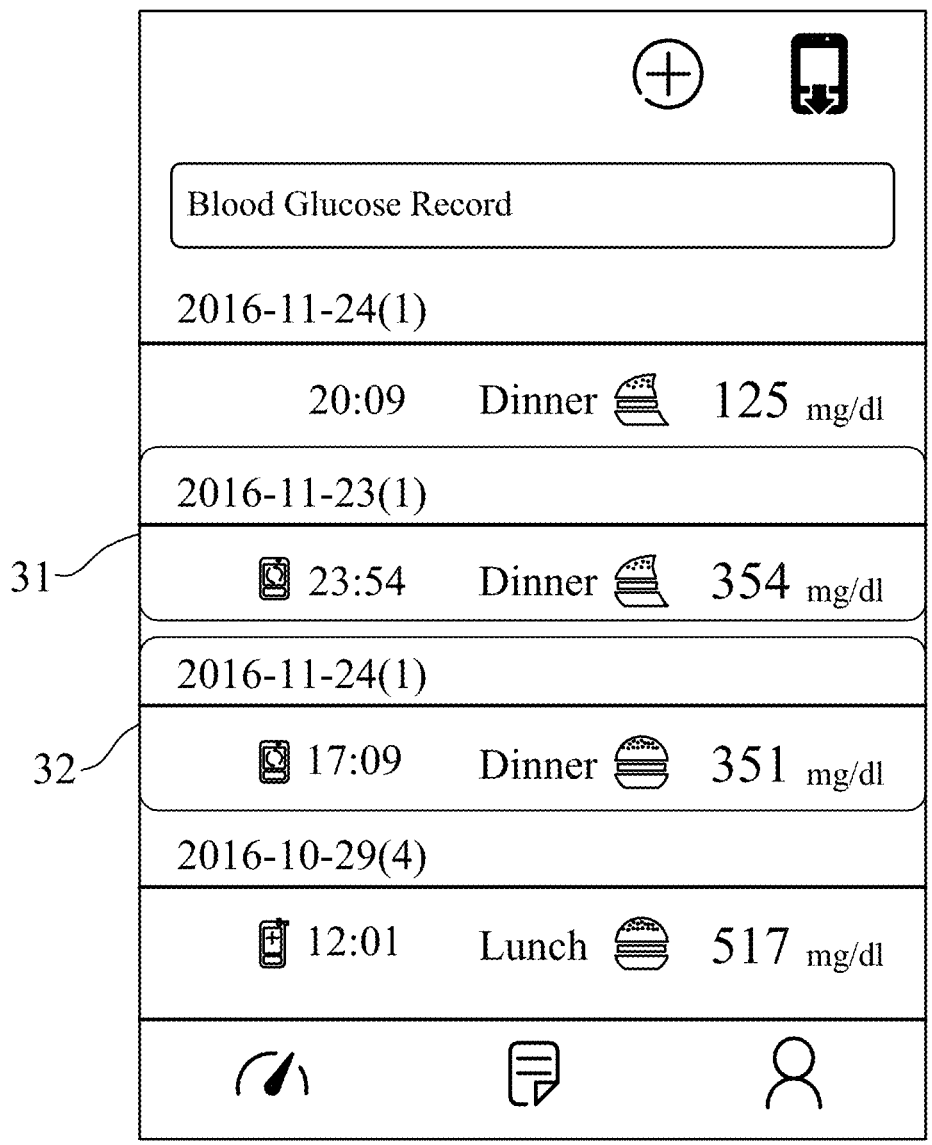
FIG. 3 shows an exemplary screen where multiple blood glucose values are arranged in order according to coordinated universal time.

As exemplified in FIG. 3, when the user or medical professionals operate the mobile device 2 or the computer terminal 14 to execute the first application or the second application, the measured blood glucose values displayed by the mobile device 2 or the computer terminal 14 are arranged in order of occurrence from bottom to top according to the respective UTC information, where the uppermost one is the latest measured blood glucose value, and the displayed measurement time is based on the local time of the blood glucose measuring device 11 when the measurement was made to facilitate checking of the measurement records by the user. As a result, for example, while the measured blood glucose value 31 is displayed above the measured blood glucose value 32 (i.e., the measurement to obtain the measured blood glucose value 31 occurred later in time than that to obtain the measured blood glucose value 32), the displayed local measurement time corresponding to the measured blood glucose value 31 appears, at face value, to be earlier than that of the measured blood glucose value 32. In one implementation, when a measured blood glucose value is transmitted to the mobile device 2, the mobile device 2 may estimate a geographical region in which the corresponding measurement is performed based on the longitude and latitude of the location of the mobile device 2, and display corresponding country information, such as a corresponding time zone, a national flag, a country name, or combinations thereof. In addition, as exemplified in FIG. 4, the first application and/or the second application may perform pairing of the measured blood glucose values based on the measurement time and the events, such as dining, exercising, medication intake, etc., to form one or more measurement pairs, and consisting of two blood glucose values respectively measured before and after lunch. In FIG. 4, when the postprandial blood glucose value is greater than the preprandial blood glucose value by over a first blood glucose threshold (e.g., 60 mg/dL), the corresponding measurement pair may be underlined in a first color (e.g., red color, see the underline (R) in FIG. 4) to indicate excessive glycemic increment; when the postprandial blood glucose value is greater than the preprandial blood glucose value by under a second blood glucose threshold (e.g., 30 mg/dL), the corresponding measurement pair may be underlined in a second color (e.g., blue color, however such condition is not shown in FIG. 4) to indicate insufficient glycemic increment; and when the postprandial blood glucose value is smaller than the preprandial blood glucose value, the corresponding measurement pair may be also underlined in the second color (see the underline (B) in FIG. 4) or in a third color (e.g., yellow color, not shown in FIG. 4) to indicate afterevent (after-meal) glycemic decrement.

Figure 5:
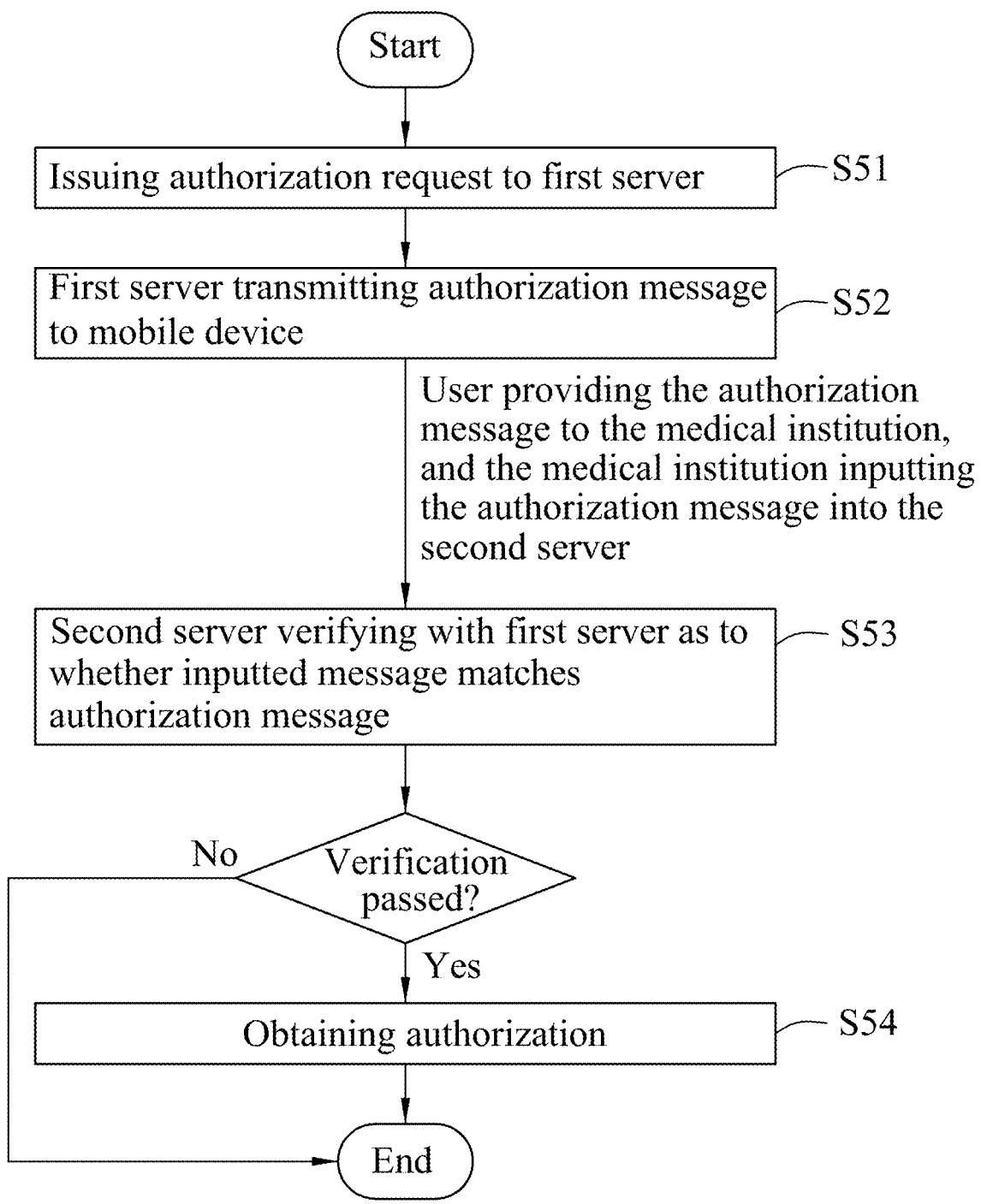
FIG. 5 is a flow chart illustrating steps of acquiring authorization to use data in a first server of the embodiment.

In one implementation, after the user uses the mobile device 2 to transmit the blood glucose values measured by the blood glucose measuring device 11 to the first server 13 via the Internet, the medical institution may, for the purpose of making diagnosis, initiate a request for authorization to use the measured blood glucose values stored in the first server 13. Referring to FIG. 5, in step S51, the medical professionals may access the second application provided by the second server 3 through the computer terminal 14 to issue an authorization request to the first server 13 for requesting sharing of the measured blood glucose values stored in the first server 13. In step S52, the first server 13 transmits, in response to receipt of the authorization request from the second server 3, an authorization message to the mobile device 2 via the Internet. The authorization message may be an authorization code transmitted in a form of a text message, but this disclosure is not limited to such implementation. If the user agrees to authorize the medical institution to utilize his/her personal data (e.g., the measured blood glucose values), the user may provide the authorization message to the medical professionals, so that the medical professionals can operate the computer terminal 14 to input the authorization message into the second server 3 via the second application. In response to receipt of the inputted message, the second server 3 verifies with the first server 13 whether the inputted message matches the authorization method (step S53), and obtains authorization when the inputted message is verified to match the authorization message transmitted by the first server 13 (step S54). On the other hand, if the user does not agree to authorize the medical institution to utilize his/her personal data and thus does not provide the authorization message to the medical professionals, or the message inputted to the second server 3 fails to pass the verification by the first server 13, the medical institution cannot obtain the authorization and cannot utilize the personal data of the user in the first server 13. In one implementation, the first server 13 may issue an authorization notification to the mobile device 2 for the user to decide whether to accept the authorization request. For example, the authorization notification may be a list of multiple candidates (e.g., medical institutions, insurance companies, pharmacies, other health-related service providers, etc.) to be selected by the user for authorization of access to the personal data. Through the user authorization mechanism, the system 1 may effectively secure the privacy of personal medical information. When the user intends to terminate the service provided by the system 1, the user may operate the first application to transmit an instruction of deletion to the first server 13 to cause the first server 13 to delete all data transmitted thereto by the user, and then, the first server 13 may issue a notification message to the second server 3 for notifying the medical institution to delete the data transmitted to the second server 3 from the first server 13 under user authorization.

In this embodiment, the second measuring apparatus 12 may be a professional blood glucose measuring device, such as a conventional POCT device Rightest® GM700 Pro and/or another biochemical instrument, which is suitable to be placed in a medical institution and is communicatively coupled to the second server 3. A backend management software may be used to implement functions such as quality management, grouping management, analysis chart generation, establishing connection to a medical advice system for the second measuring apparatus 12, etc. When the user goes to the medical institution, the medical professionals may perform measurements of the glycated hemoglobin level (second physiological parameter) and the blood glucose level of the user using the second measuring apparatus 12, and transmit the measured glycated hemoglobin value (second parameter value) and blood glucose value to the first server 13 via the second server 3. In the case that the user has authorized the medical institution to use the personal data in the first server 13, further authorization may not be necessary when the second server 3 transmits the measured glycated hemoglobin value and blood glucose value to the first server 13. In one implementation, the medical professionals may use the computer terminal 14 to manually input the measured glycated hemoglobin value measured by the biochemical instrument via the second application, and then the second server 3 transmits the measured glycated hemoglobin value to the first server 13. In one implementation, the second measuring apparatus 12 is capable of connecting to the first server 13 through the Internet, so that the glycated hemoglobin value and blood glucose value measured by the second measuring apparatus 12 may be directly transmitted to the first server 13. It is noted that the computer terminal 14 may be any type of computing device such as a desktop computer, a notebook computer, a tablet computer, a smartphone, etc., and this disclosure is not limited in this respect.

The first server 13 or the second server 3 may calculate an estimated glycated hemoglobin value based on a set of blood glucose values measured within a time segment, and output a signal indicating the estimated glycated hemoglobin value and/or the measured glycated hemoglobin value to the mobile device 2 or the second server 3 for use by the first application or the second application. Accordingly, the user may use the mobile device 2 to get the measured glycated hemoglobin values and track variation of the estimated glycated hemoglobin value by himself/herself, and the medical professionals may observe and analyze all the user data measured by the blood glucose measuring device 11 and the second measuring apparatus 12 with the user's permission, thereby comprehensively evaluate the health condition of the user. In this embodiment, the glycated hemoglobin level serves as an important index for blood glucose control, but in other embodiments, another index substance may be used in place of or in addition to the glycated hemoglobin level in evaluating the health condition of the user, and this disclosure is not limited to this respect.

In this embodiment, the first server 13 calculates a blood glucose average of the measured blood glucose values, and calculates the estimated glycated hemoglobin value based on the blood glucose average.

As an example, the estimated glycated hemoglobin value is calculated according to a formula of $$E_{HbAlc}=(A_{Glucose}+P_1)/P_2$$

where $E_{HbAlc}$ represents the estimated glycated hemoglobin value, $A_{Glucose}$ represents the blood glucose average, $P_1$ is a first parameter ranging between 43 and 48, and $P_2$ is a second parameter ranging between 25 and 30.

For instance, FIG. 6 illustrates a screen displayed on the mobile device 2 or the computer terminal 14 by executing the first application or the second application. The screen shows the glycated hemoglobin value measured by the second measuring apparatus 12, the blood glucose values measured by the blood glucose measuring device 11 and/or the second measuring apparatus 12, and the estimated glycated hemoglobin value calculated by the first server 13. In this instance, the user used the second measuring apparatus 12 to measure the glycated hemoglobin level in the medical institution, and obtained the measured glycated hemoglobin values of 6.6% and 6.3% respectively on Jan. 1 and Apr. 1, 2016. When one of the measured glycated hemoglobin values is selected, the application may display the blood glucose values measured within a time segment tracing back from the date on which the selected glycated hemoglobin value is measured. For example, when the glycated hemoglobin value measured on Jan. 1, 2016 is selected, all of the blood glucose values measured in the past 90 days as of Jan. 1, 2016 may be listed in a table shown in the right part of the screen for reference by the user or the medical professionals. In this embodiment, the application calculates the estimated glycated hemoglobin value every week based on the blood glucose values measured by the blood glucose measuring device 11 and/or the second measuring apparatus 12 in the past 7 days, but this disclosure is not limited to such implementation. In other embodiments, the estimated glycated hemoglobin values may be calculated based on the blood glucose values measured in the past 14 days, 30 days or other desired number of days.

In FIG. 6, the user used the blood glucose measuring device 11 and/or the second measuring apparatus 12 to measure the blood glucose level fifteen times from Apr. 1 to Apr. 7, 2016 and thirty two times from Apr. 8 to Apr. 14, 2016, and the first server 13 calculates the estimated glycated hemoglobin values of 6.1% and 5.7% respectively for the two time segments. Accordingly, by use of the system 1 according to this disclosure, the user may track his/her glycated hemoglobin variation by observing the estimated glycated hemoglobin values which are calculated every week even if he/she uses the professional second measuring apparatus 12 to measure the glycated hemoglobin only once every three months. In addition, the mobile device 2 or the second server 3 may output a notification message through the first application or the second application when a difference between the estimated glycated hemoglobin value and the measured glycated hemoglobin value is greater than a threshold value (e.g., ranging between 1.5% and 3%), so that the user or the medical professionals may notice abnormal variation of the glycated hemoglobin level in time. Even if there is no abnormal variation in the glycated hemoglobin level, the estimated glycated hemoglobin values can still serve as reference information for a doctor to make diagnosis. In one embodiment, the mobile device 2 may directly calculate the estimated glycated hemoglobin values via the first application based on the blood glucose values measured by the blood glucose measuring device 11.

In addition to the estimation and management of the blood glucose level, the system 1 according to this disclosure further provides statistical analysis and management for the blood glucose level. In detail, the first server 13 calculates an average and a standard deviation of the blood glucose values measured within a time segment. When the standard deviation is greater than a first product of the average and a first factor (e.g., ranging between 0.2 and 1 or between 0.3 and 0.6), the first server 13 may output first information indicating excessive fluctuation in blood glucose level; when the standard deviation is smaller than a second product of the average and a second factor (e.g., ranging between 0.1 and 0.7 or between 0.2 and 0.4) which is smaller than the first factor, the first server 13 may output second information indicating ideal fluctuation in blood glucose level; and when the standard deviation is between the first product (of the average and the first factor) and the second product (of the average and the second factor), the first server 13 may output third information indicating large (but not excessive) fluctuation in blood glucose level. In one embodiment, the mobile device 2 may acquire the blood glucose values from the first server 13 to perform the abovementioned statistical analysis and management for the blood glucose level.

Figure 7:
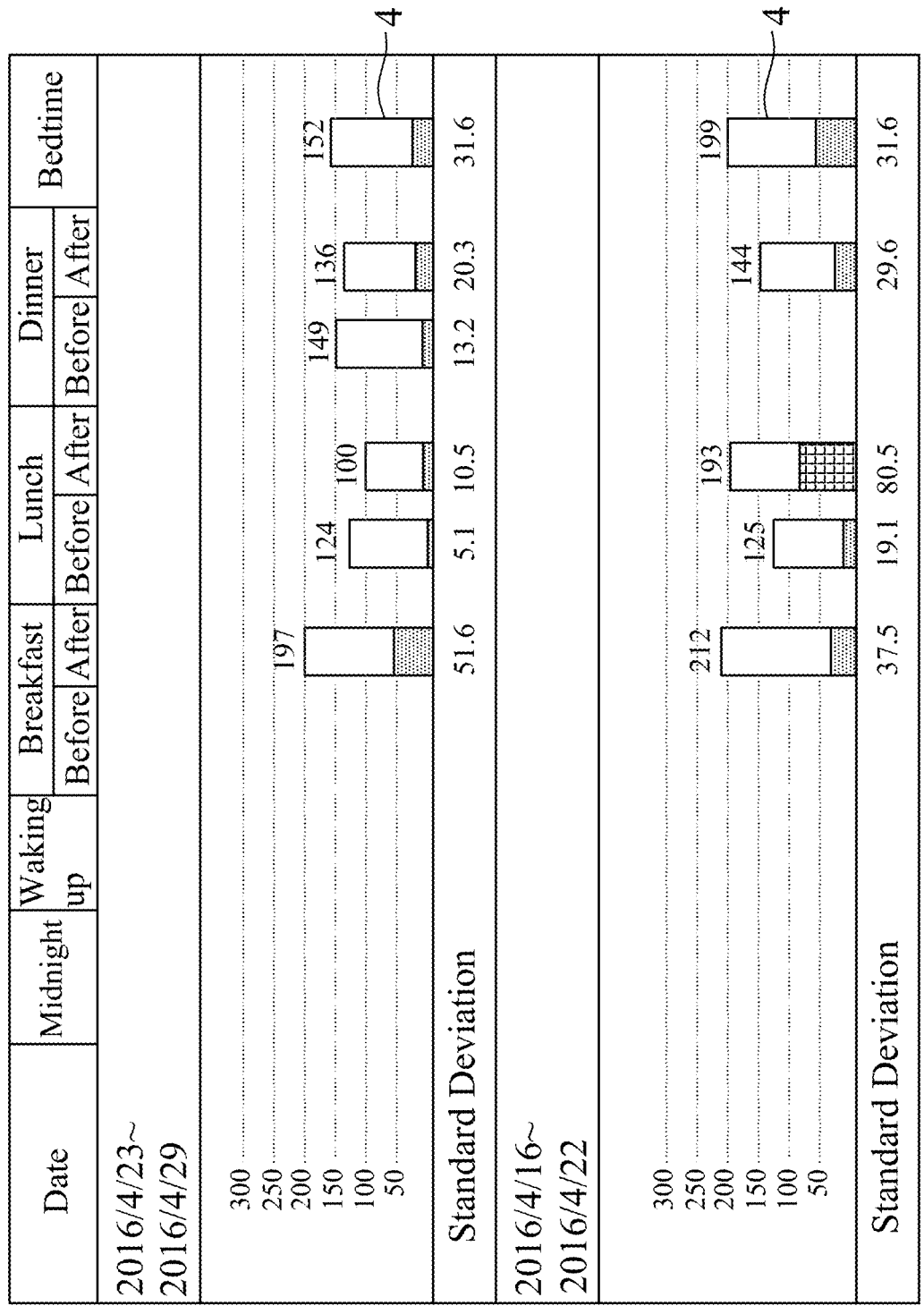
FIGS. 7 to 9 are plots to be displayed by the mobile device, showing multiple vertical bar indicators indicating blood-glucose-related information, and illustrating relevant operation to display a message box associated with a selected vertical bar indicator.
Figure 8:
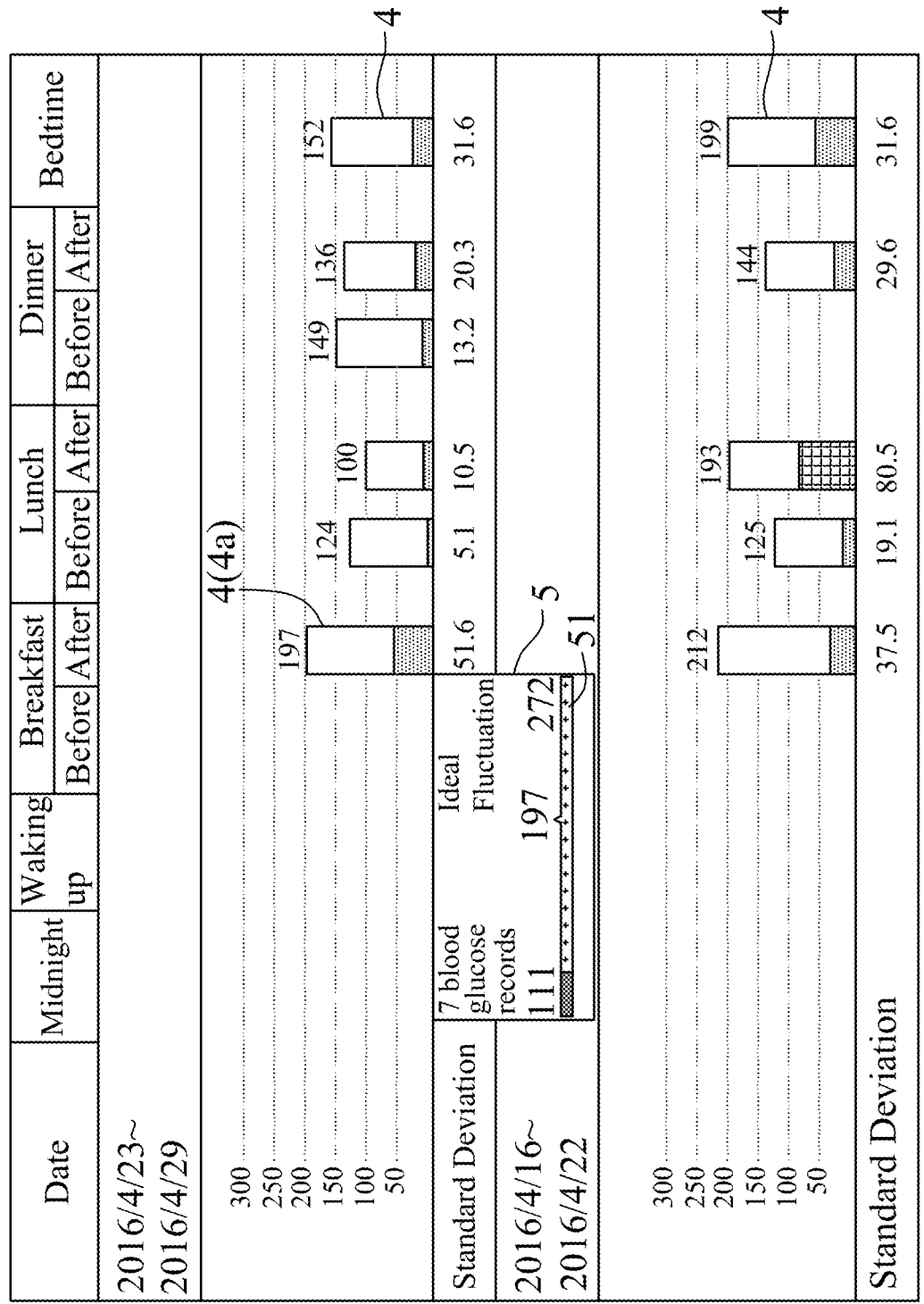
Figure 9:
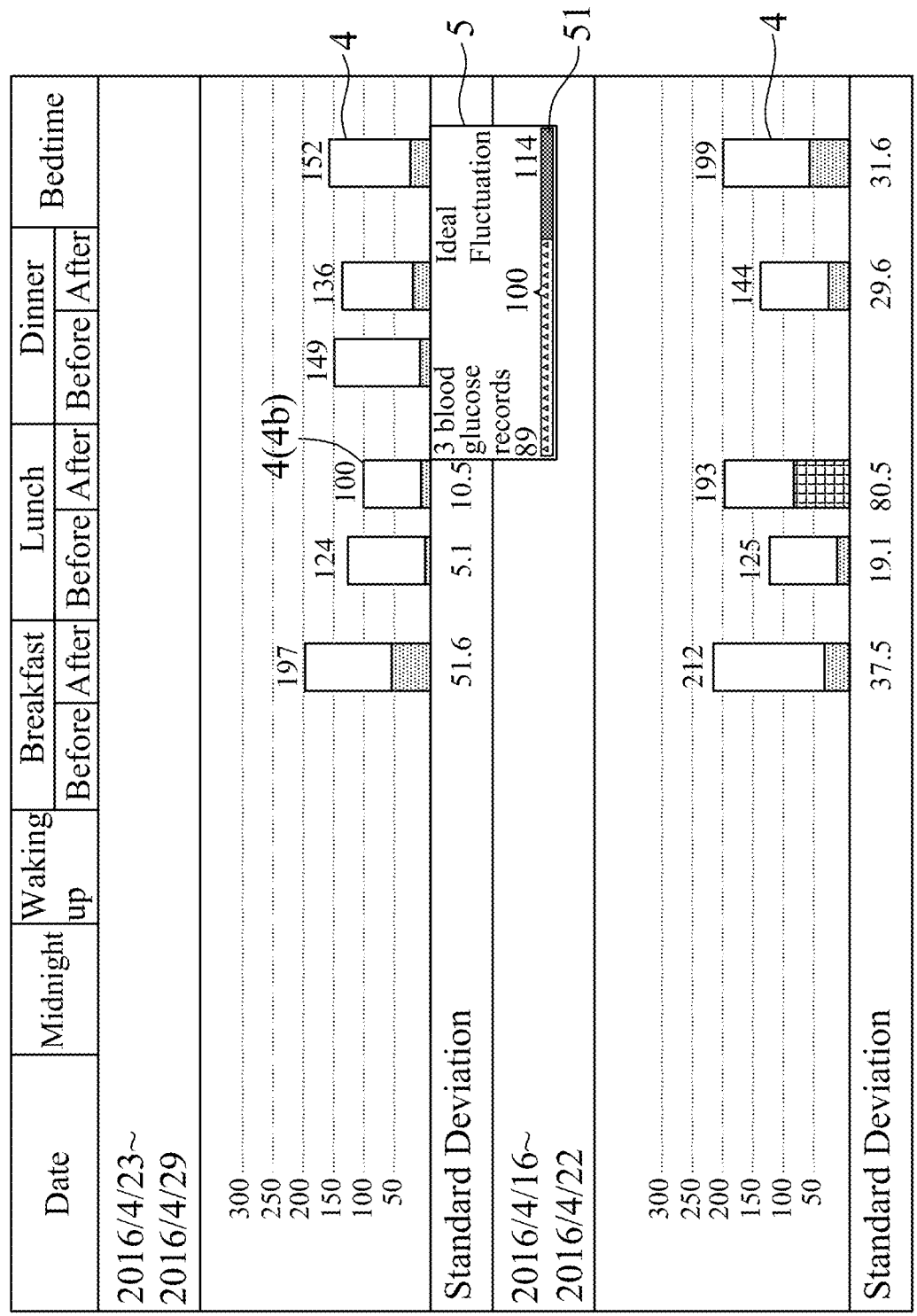

Referring to FIGS. 7 to 9, the statistical analysis may be performed by applications executed by the mobile device 2, the computer terminal 14, or the authorized device 7 that are connected to the first server 13 (e.g., the first application, the second application, etc.), and displayed on a display device, which may be a part of the mobile device 2, the computer terminal 14 or the authorized device 7, to visually output data management information associated with the measured blood glucose values in a form of a plot. In this embodiment, the statistical analysis result is displayed in a graphical user interface that is generated by the application, and that includes a vertical bar chart 4, and a message block 5 showing a horizontal bar chart 51.

As exemplified in FIG. 7, the plot outputted by the graphical user interface includes a horizontal axis to represent (predetermined) event labels each of which may be associated with a specific category and may be user defined (e.g., by selecting one of a plurality of the predetermined event labels) to correspond to the measured blood glucose values, and a vertical axis to represent the average and the standard deviation of the measured blood glucose values. The categories for the predetermined event labels may include, but not limited to, a category of midnight, a category of waking up, a category of before breakfast, a category of after breakfast, a category of before lunch, a category of after lunch, a category of before dinner, a category of after dinner, a category of before bedtime, a category of before exercise, a category of after exercise, a category of before medication intake and a category of after medication intake. The after-breakfast blood glucose values measured during the period of from April 23 to Apr. 29, 2016 have an average of 197 mg/dL indicated by an average bar indicator with a height corresponding to the average, and a standard deviation of 51.6 indicated by a standard-deviation bar indicator which has a height corresponding to the standard deviation and which is included in the average bar indicator. In this time segment, since the standard deviation is smaller than a second product based on the average, the standard-deviation bar indicator is displayed as a dotted bar to indicate ideal fluctuation in blood glucose level. The after-lunch blood glucose values measured during the period of from Apr. 16 to Apr. 22, 2016 have an average of 193 mg/dL and a standard deviation of 80.5, which is between the first product and the second product based on the average, so the standard-deviation bar indicator is displayed with "L" patterns to indicate large fluctuation in blood glucose level. When the standard deviation of a set of the blood glucose values measured within a time segment is greater than the first product based on the average of the same set of the blood glucose values, the standard-deviation bar indicator is displayed in yet another form to indicate excessive fluctuation in blood glucose level. In one implementation, different colors, such as green, orange and red colors may be used for the standard-deviation bar indicator to represent "ideal fluctuation", "large fluctuation" and "excessive fluctuation" in blood glucose level, respectively, but this disclosure is not limited in this respect, as long as the abovementioned three conditions are visually distinguishable from each other in the plot. In addition, the length of the time segment in which to accumulate data for calculating the average and the standard deviation may be adjusted as being, for example, a month, a year, or any other desired number of days.

In FIGS. 8 and 9, when a bar indicator 4 is selected by the user or the medical professionals through operation on the corresponding application of the mobile device 2 or the computer terminal 14, the graphical user interface further provides a message block 5 that corresponds to the selected bar indicator and that contains information of a number of blood glucose measurements, a fluctuation condition and a horizontal bar indicator 51. The horizontal bar indicator 51 has two ends respectively indicating a maximum measured blood glucose value and a minimum measured blood glucose value, and an inner mark indicating the blood glucose average. Further, the horizontal bar indicator 51 may include multiple parts to indicate the ratios of the number of normal measured blood glucose values, the number of excessively high measured blood glucose values, and the number of excessively low measured blood glucose values to the total number of measured blood glucose values, respectively. For example, the part corresponding to the normal measured blood glucose values is represented in the gray color as shown in FIGS. 8 and 9; the part corresponding to the excessively high measured blood glucose values is represented by cross marks as shown in FIG. 8, and the part corresponding to the excessively low measured blood glucose values is represented by triangle marks as shown in FIG. 9. However, this disclosure is not limited in this respect, and the different parts of the horizontal bar indicator 51 may be represented in different colors in other embodiments. For example, the part corresponding to the excessively high measured blood glucose values may be represented in the red color, and the part corresponding to the excessively low measured blood glucose values may be represented in the blue color.

As exemplified in FIG. 8, when the bar indicator 4a is selected, the corresponding message block 5 is displayed and illustrates that there are seven pieces of after-breakfast blood glucose values measured in the time segment of between Apr. 23 and Apr. 29, 2016 with a minimum of 111 mg/dL, a maximum of 272 mg/dL and an average of 197 mg/dL, that the fluctuation in blood glucose level is ideal, and that some of the blood glucose values are excessively high, and it can be observed that the ideal fluctuation results from the majority of the blood glucose values that are excessively high blood glucose values. As exemplified in FIG. 9, when the bar indicator 4b is selected, the corresponding message block 5 is displayed and illustrates that there are three pieces of after-lunch blood glucose values measured in the time segment of between Apr. 23 and Apr. 29, 2016 with a minimum of 89 mg/dL, a maximum of 114 mg/dL and an average of 100 mg/dL, that the fluctuation in blood glucose level is ideal, and that some of the blood glucose values are excessively low, and it can be observed that the ideal fluctuation results from the majority of the blood glucose values that are excessively low blood glucose values. By virtue of the message block 5, the user may easily monitor his/her blood glucose condition, preventing exacerbation of the illness.

Figure 10:
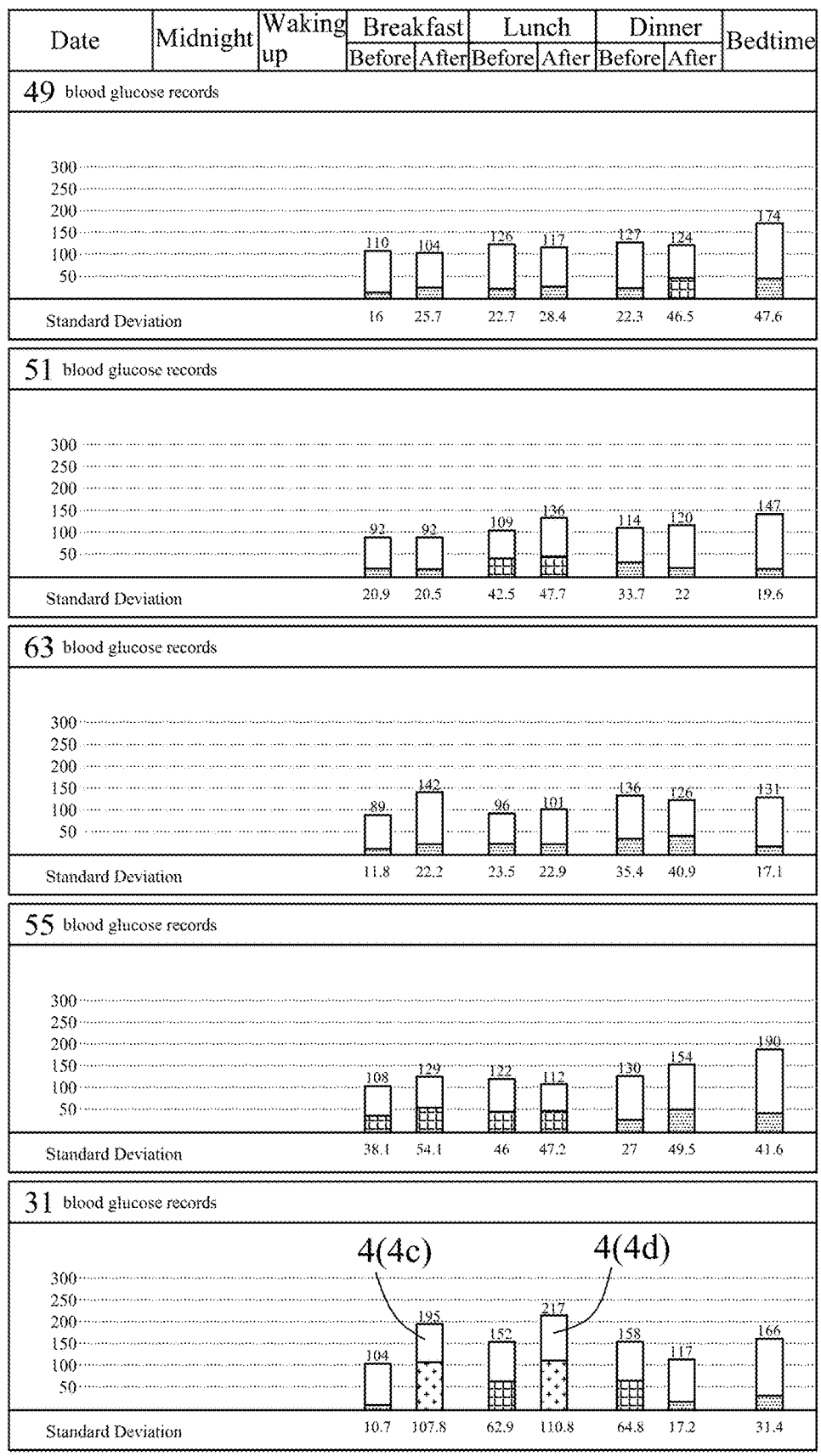
FIG. 10 is a plot illustrating multiple sets of the blood glucose values measured in different time segments.

FIG. 10 exemplifies a screen that shows multiple plots illustrating statistical analysis results of statistical analysis made upon the blood glucose data recorded by a user who uses the system 1 according to this disclosure. The statistical analysis and the graphical user interface may facilitate the medical professionals to make diagnosis more effectively. In FIG. 10, the statistics of the measured blood glucose data are arranged from bottom to top in chronological order, where the lower plots correspond to relatively old data and the upper plots correspond to relatively new data. After the user uses the system 1 to monitor his/her blood glucose level, it can be observed from these plots that the after-breakfast blood glucose values and the after-lunch blood glucose values have gradually improved from "excessive fluctuation" (represented by cross marks, see the bar indicators 4c and 4d in FIG. 10) to "ideal fluctuation" (represented by dots).

Figure 11:
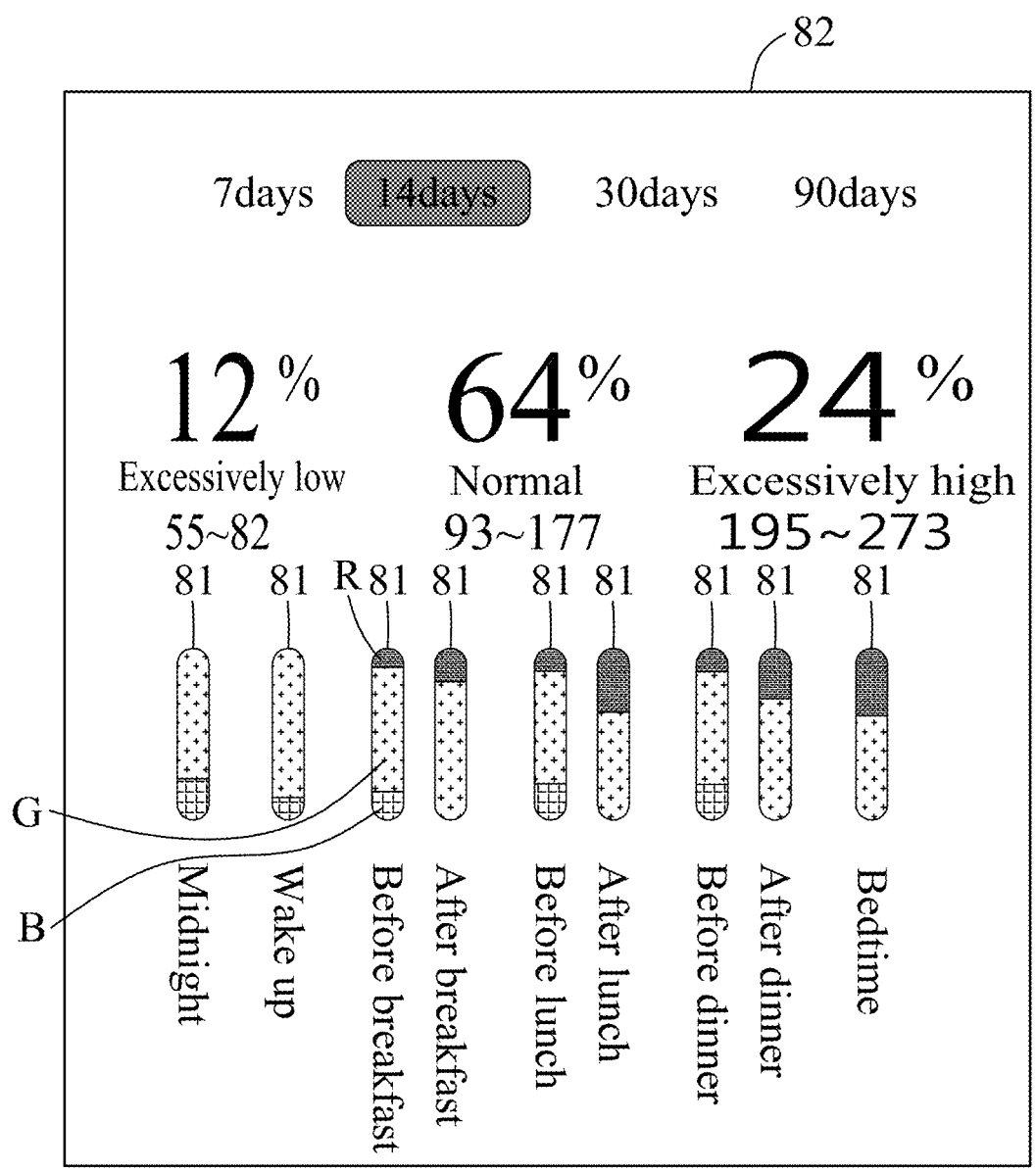
FIG. 11 is a plot illustrating a plurality of ratio indicators respectively corresponding to different event labels for the measured blood glucose values according to this disclosure.

Referring to FIG. 11, in one implementation, the first server 13, the second server 3, the mobile device 2 or the computer terminal 14 may determine, for a specific time period, each of the measured blood glucose values that correspond to the same event label and that are measured within the specific time period as being an excessively-high measured blood glucose value, a normal measured blood glucose value or an excessively-low measured blood glucose value based on a predetermined criterion. Then, for the specific time period, the first server 13, the second server 3, the mobile device 2 or the computer terminal 14 may calculate, for each of the event labels, a first ratio of a number of the corresponding excessively-high measured blood glucose values to a total number of the corresponding measured blood glucose values, a second ratio of a number of the corresponding normal measured blood glucose values to the total number of the corresponding measured blood glucose values, and a third ratio of a number of the corresponding excessively-low measured blood glucose values to the total number of the corresponding measured blood glucose values, and generate a ratio indicator that indicates the first, second and third ratios corresponding to the event label and that is to be displayed on the display device.

According to Standards of Medical Care in Diabetes published by the American Diabetes Association (ADA), for the postprandial conditions (e.g., after breakfast, after lunch or after dinner) and at midnight, the blood glucose level ranging between 70 mg/dL and 140 mg/dL would be considered normal, the blood glucose level greater than 140 mg/dL would be considered excessively high, and the blood glucose level smaller than 70 mg/dL would be considered excessively low; for the preprandial conditions (e.g., before breakfast, before lunch or before dinner) and at the time of waking up, the blood glucose level ranging between 70 mg/dL and 100 mg/dL would be considered normal, the blood glucose level greater than 100 mg/dL would be considered excessively high, and the blood glucose level smaller than 70 mg/dL would be considered excessively low; and for the condition of before bedtime, the blood glucose level ranging between 70 mg/dL and 120 mg/dL would be considered normal, the blood glucose level greater than 120 mg/dL would be considered excessively high, and the blood glucose level smaller than 70 mg/dL would be considered excessively low. In practice, the ranges used to determine normality/abnormality of the blood glucose level may vary based on the doctor's diagnosis for the patient.

The ratio indicator may be presented in a form of a vertical bar, a circle, a horizontal bar, a ring, a radar chart, etc., but this disclosure is not limited in this respect. In FIG. 11, each of the ratio indicators is presented in a form of a vertical bar. For each event label, the corresponding ratio indicator may include a first segment that is presented in a first format and that has a first size in a specific dimension (e.g., a length) to represent the first ratio, a second segment that is presented in a second format and that has a second size in the specific dimension to represent the second ratio, and a third segment that is presented in a third format and that has a third size in the specific dimension to represent the third ratio. In this embodiment, the ratio of a length of each of the first, second and third segments to a length of the ratio indicator is identical to the respective one of the first, second and third ratios. It is noted that the first, second and third formats may be different patterns, colors, etc., and this disclosure is not limited in this respect. In case that the ratio indicator is presented as a vertical bar, if the first, second and third ratios are all greater than zero, the first segment is adjacent to the second segment, the second segment is adjacent to the third segment, and the first segment is separate from the third segment by the second segment (i.e., the second segment is between the first and third segments).

In one implementation as exemplified in FIG. 11, for each ratio indicator 81, the first segment (R), the second segment (G) and the third segment (B) may be colored respectively in red, green and blue, which are respectively represented by different marks for illustrative purposes. By virtue of the ratio indicators 81, the user may clearly identify, from FIG. 11, that in the last 14 days, the excessively high blood glucose level occurred relatively often before and after meals and before bedtime, particularly after lunch, after dinner and before bedtime, and that the excessively low blood glucose level occurred relatively often at midnight, upon waking up and before meal, particularly at midnight. Through the ratio indicators 81, the user may easily become aware of the events or time segments where the blood glucose level may be excessively high or low, so as to be motivated to adjust his/her life style.

In addition to displaying the event labels and the corresponding ratio indicators 81, a screen 82 displayed by the display device further shows, based on a total number of the blood glucose values measured within a specific duration (e.g., the last 14 days), the ratios of the number of the excessively-high measured blood glucose values, the number the normal measured blood glucose values and the number the excessively-low measured blood glucose values to the total number of the measured blood glucose values, which are 24%, 64% and 12%, respectively, and indications that the excessively-high measured blood glucose values are distributed within a swing range of between 195 mg/dL and 273 mg/dL, the normal measured blood glucose values are distributed within a swing range of between 93 mg/dL and 177 mg/dL, and the excessively-low measured blood glucose values are distributed within a swing range of between 55 mg/dL and 82 mg/dL. The severity of the blood glucose abnormality may be determined from the ranges within which the measured blood glucose values are distributed.

Even if the concentration of glycated hemoglobin is normal, high blood glucose variation may still lead to diabetic complications. Accordingly, the swing of the blood glucose level is preferred to be steadily controlled within a small range, which is an object of diabetic care. Displaying of the blood glucose swing ranges may assist the user in noticing the abnormality degree of the blood glucose level.

In addition, the user may track his/her blood glucose conditions via the ratio indicator(s) 81 based on a desired unit of time (e.g., causing 14 days to serve as a unit of time). For instance, assuming that a ratio indicator that corresponds to a time period between 28 days prior and 15 days prior and that corresponds to the condition of waking up shows all the measured blood glucose values being normal, and a ratio indicator that corresponds to a time period between 14 days prior and 1 day prior and that corresponds to the condition of waking up shows high ratio in the excessively low blood glucose values, the user or medical professionals may thus determine that the blood glucose level was abnormal in the past 14 days, and may further analyze the reason causing such abnormality and decide on a plan/treatment for controlling the blood glucose accordingly. The unit of time may be set as desired, such as 7 days, 30 days or any desired number of days, and this disclosure is not limited in this respect.

Figure 12:
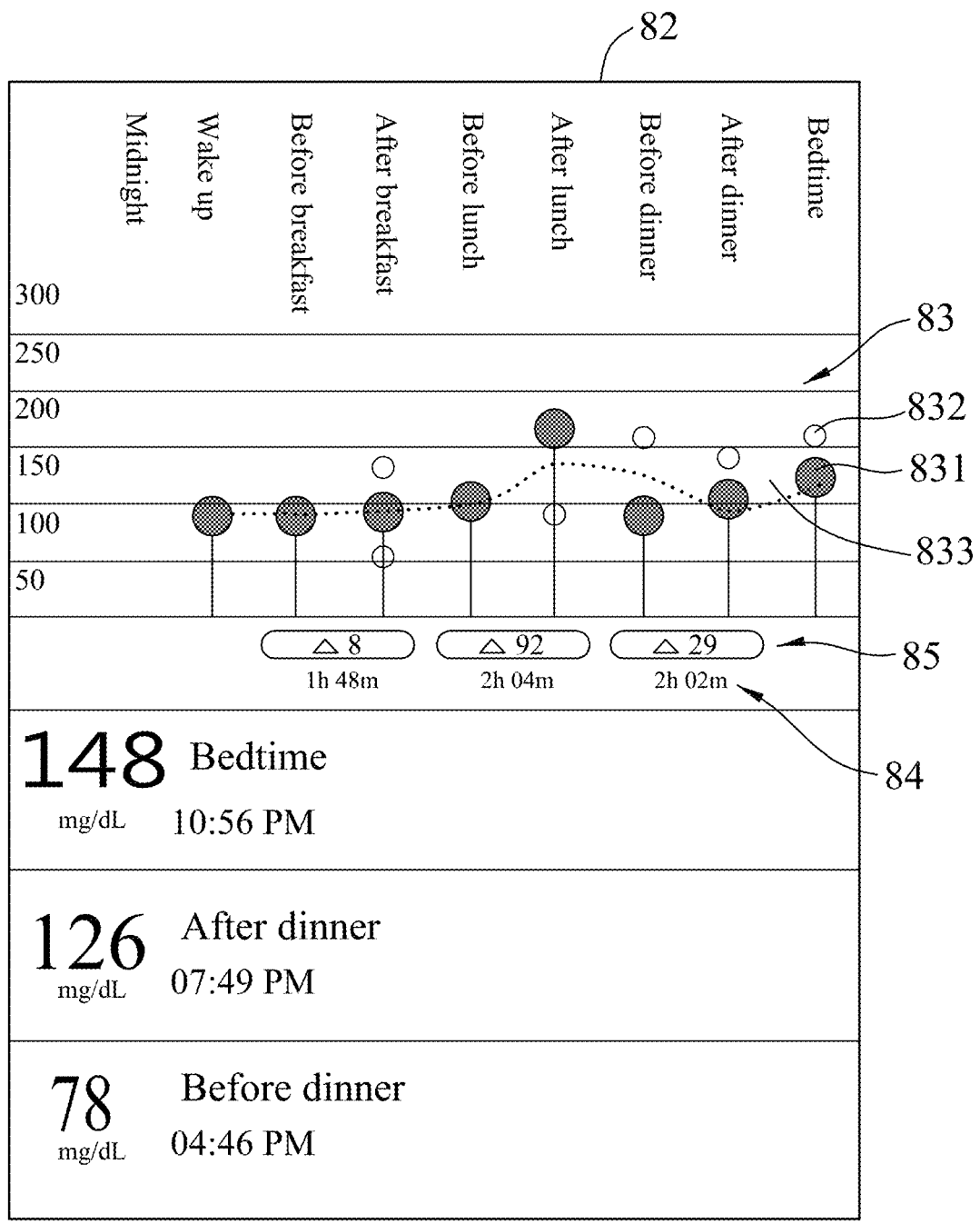
FIG. 12 is a plot illustrating a run chart for the measured blood glucose values according to this disclosure.

Referring to FIG. 12, the first server 13, the second server 3, the mobile device 2 or the computer terminal 14 may further generate a run chart 83 which corresponds to one day (e.g. a user-selected day) and which is to be displayed on the display device. For each of the event labels in the run chart 83, a first mark (e.g., the solid circle mark 831) is used to represent a latest measured blood glucose value among all of the blood glucose values that are measured on that day and that correspond to the event label, and a second mark (e.g., the hollow circle mark 832) is used to represent a blood glucose value that is measured on that day, that corresponds to the event label and that is not the latest measured blood glucose value. Each blood glucose value that is measured on that day but not the latest measured blood glucose value is represented by an individual second mark. When the user operates the mobile device 2 or the computer terminal 14 to select the first mark 831 or the second mark 832, the screen 82 may further show measurement information associated with the selected mark, such as the measured blood glucose value, the measurement time at which the measurement is performed. In FIG. 12, the screen 82 further shows additional two pieces of measurement information that are closest to and prior than the measurement information corresponding to the selected mark in terms of time. The run chart 83 may further include a simple moving average line 833 which corresponds to the event labels and which is a curve indicating, for each of the event labels, an average value of some of the measured first parameter values of the first marks 831 that correspond to the event label. For example, a value represented by the simple moving average line 833 under the event label "After lunch" may be an average value of the measured first parameter values corresponding to the first marks 831 respectively under the event labels "After lunch" and "Before lunch", and a value represented by the simple moving average line 833 under the event label "Before dinner" may be an average value of the measured first parameter values corresponding to the first marks 831 respectively under the event labels "Before dinner" and "After lunch". A number of the measured first parameter values used to calculate an average value under an event label may be defined by the user, and this disclosure is not limited in this respect. In addition, the screen 82 further shows measurement differences (e.g. a difference of the measured blood glucose values, a difference of measurement time points at which the corresponding measurements are performed) between the measurements respectively corresponding to the relevant event labels that are adjacent to each other in terms of time (e.g., the event labels of before and after breakfast, lunch or dinner). As exemplified in FIG. 12, the reference number 84 refers to a time difference between two measurements respectively performed before and after dinner being 2 hour and 2 minutes, and the reference number 85 refers to a blood glucose increment between the two measurements respectively performed before and after dinner being 29 mg/dL.

In summary, by virtue of the system 1 that may calculate the estimated glycated hemoglobin value based on the measured blood glucose values to be used with the glycated hemoglobin value measured by the professional second measuring apparatus 12 as references, and provide statistical analysis and management function of the measured blood glucose values through the first server 13 and the second server 3, the user may periodically track variation of the glycated hemoglobin level and the blood glucose level.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A system for monitoring a physiological condition of a user, comprising:
  a first apparatus for personal use including a first measuring device configured to measure a first physiological parameter of the user, and to generate a first parameter signal indicating a measured first parameter value of the first physiological parameter measured thereby;
  a second apparatus for use by medical professionals including a second measuring device configured to measure a second physiological parameter of the user, and to generate a second parameter signal indicating a measured second parameter value of the second physiological parameter measured thereby;

a first server communicatively coupled to said first apparatus via a network for receiving the first parameter signal therefrom, and disposed to receive the second parameter signal via the network; and a second server placed in a medical institution, and configured to transmit, in response to an operation of a medical professional, an authorization request to said first server for requesting use of the measured first parameter value received by said first server;

wherein each of the measured first and second parameter values is associated with a disease condition, a health condition, a nutrient intake condition, a fitness condition or an exercise condition of the user;

wherein said first server is configured to transmit, in response to receipt of the authorization request from said second server, an authorization message to said first apparatus; and wherein said second server is further configured to verify with said first server, in response to receipt of an input message, whether the input message matches with the authorization message, and to obtain authorization when the input message is verified to match the authorization message by said first server.

2. The system according to claim 1, wherein the first physiological parameter is blood glucose level, and the second physiological parameter is glycated hemoglobin level.

3. The system according to claim 2, wherein said first server is configured to calculate an estimated second parameter value of glycated hemoglobin level based on a set of measured first parameter values of blood glucose level, and to output the estimated second parameter value and the measured second parameter value of glycated hemoglobin level to at least one application provided by said first server.

4. The system according to claim 3, wherein said first server is configured to calculate a blood glucose average of the set of measured first parameter values of blood glucose level, and to calculate the estimated second parameter value of glycated hemoglobin level based on the blood glucose average, wherein the estimated second parameter value is positively correlated to the blood glucose average.

5. The system according to claim 3, wherein said first server is further configured to transmit to said at least one application a signal indicating the estimated second parameter value and the measured second parameter value, and said at least one application is configured to output a notification message when a difference between the estimated second parameter value and the measured second parameter value is greater than a threshold value.

6. The system according to claim 2, wherein said second apparatus is further configured to additionally measure the first physiological parameter of the user, and to generate a third parameter signal indicating an additionally measured first parameter value of the first physiological parameter measured thereby, and said first server further receives the third parameter signal from said second apparatus; and wherein said first server is further configured to perform statistical analysis on either of the measured and additionally measured first parameter values measured respectively by said first apparatus and said second apparatus.

7. The system according to claim 6, wherein the statistical analysis performed by said first server includes:

calculating an average and a standard deviation of the measured or additionally measured first parameter values;

outputting first information indicating excessive fluctuation in blood glucose level when the standard deviation is greater than a first product of the average and a first factor;

outputting second information indicating ideal fluctuation in blood glucose level when the standard deviation is smaller than a second product of the average and a second factor which is smaller than the first factor; and outputting third information indicating large fluctuation in blood glucose level when the standard deviation is between the first product and the second product of the average.

8. The system according to claim 7, further comprising a computer terminal placed in the medical institution, wherein at least one of said first apparatus and said computer terminal is configured to generate a graphical user interface that visually outputs a plot including a horizontal axis to represent event labels corresponding to the measured or additionally measured first parameter values, a vertical axis to represent the average and the standard deviation of the measured or additionally measured first parameter values, an average indicator to indicate a value of the average, and a standard deviation indicator to indicate a value of the standard deviation, wherein at least a portion of the standard deviation indicator is included within the average indicator.

9. The system according to claim 1, wherein the first apparatus comprises a mobile device configured to transmit local time information to said first measuring device for synchronization of said mobile device and said first measuring device in terms of time;

wherein said first measuring device is further configured to transmit to said mobile device a measurement signal indicating the measured first parameter value and a data sequence that corresponds to the measured first parameter value and that includes information of a local measurement time point at which the measured first parameter value is acquired; and wherein said mobile device is configured to store, in response to receipt of the measurement signal, a measurement data piece including the measured first parameter value, the data sequence, and coordinated universal time information corresponding to the local measurement time point.

10. The system according to claim 9, wherein, when said mobile device stores two or more of the measurement data pieces each corresponding to a respective local measurement time point, said mobile device displays the measured first parameter values of the measurement data pieces in chronological order based on the coordinated universal time information.

11. The system according to claim 1, wherein one of said first server and said first apparatus is:

operable to define an event label for the measured first parameter value of the first physiological parameter, and further configured, when said first apparatus is used to measure the first physiological parameter of the user multiple times to acquire a plurality of the measured first parameter values of the first physiological parameter each of which corresponds to one of a plurality of predetermined event labels, to determine, for at least one of the predetermined event labels, each of the measured first parameter values that correspond to said at least one of the predetermined event labels to be one of an excessively-high measured value, a normal measured value and an excessively-low measured value based on a predetermined criterion,
to calculate, for said at least one of the predetermined event labels, a first ratio of a number of the excessively-high measured values to a total number of the measured first parameter values, a second ratio of a number of the normal measured values to the total number of the measured first parameter values, and a third ratio of a number of the excessively-low measured values to the total number of the measured first parameter values, and
to generate, for said at least one of the predetermined event labels, a ratio indicator that includes a first segment presented in a first format and having a first size in a specific dimension, a second segment presented in a second format and having a second size in the specific dimension, and a third segment presented in a third format and having a third size in the specific dimension, wherein a ratio of the first size to a size of the ratio indicator in the specific dimension is identical to the first ratio, a ratio of the second size to the size of the ratio indicator in the specific dimension is identical to the second ratio, and a ratio of the third size to the size of the ratio indicator in the specific dimension is identical to the third ratio;
said system further comprising a display device coupled to said one of said first server and said first apparatus, and configured to display the ratio indicator for said at least one of the predetermined event labels.

12. The system according to claim 11, wherein, when each of the first, second and third ratios is greater than zero, the first segment is adjacent to the second segment, the second segment is adjacent to the third segment, and the second segment is between the first and third segments.

13. The system according to claim 11, wherein said one of said first server and said first apparatus is further configured to generate a run chart that indicates the measured first parameter values in relation to the predetermined event labels;
wherein said display device is further configured to display the run chart.

14. The system according to claim 13, wherein the run chart further includes a simple moving average line which corresponds to the predetermined event labels and which is a curve indicating, for each of the predetermined event labels, an average value of the measured first parameter values that correspond to the predetermined event label.

15. The system according to claim 13, wherein, in the run chart, for each of the predetermined event labels, a latest one of the measured first parameter values that correspond to the predetermined event label is represented by a first mark, and each of the measured first parameter value or values that corresponds to the predetermined event label and is other than the latest one of the measured first parameter values is represented by a second mark that is different from the first mark.

16. A system for monitoring a physiological condition of a user, comprising:
a first apparatus for personal use including a device configured to measure a blood glucose level of the user, and to generate a first parameter signal indicating a measured blood glucose value of the blood glucose level measured thereby;
a second apparatus for use by medical professionals including a device configured to measure a glycated hemoglobin level of the user, to generate a second parameter signal indicating a measured glycated hemoglobin value of the glycated hemoglobin level measured thereby, to measure the blood glucose level of the user, and to generate a third parameter signal indicating a measured blood glucose value of the blood glucose level measured thereby; and
a first server communicatively coupled to said first apparatus via a network for receiving the first parameter signal therefrom, and disposed to receive the second and third parameter signals via the network, and configured to calculate an estimated glycated hemoglobin value based on a set of the measured blood glucose values measured by said first apparatus and said second apparatus, and to transmit to at least one application provided by said first server a signal indicating the estimated glycated hemoglobin value and the measured glycated hemoglobin value;
wherein said at least one application is further configured to compare the estimated glycated hemoglobin value and the measured glycated hemoglobin value, and to visually output a notification message when a difference between the estimated glycated hemoglobin value and the measured glycated hemoglobin value is greater than a threshold value.

17. The system according to claim 16, wherein said first server is configured to calculate an average and a standard deviation of the set of the measured blood glucose values;
wherein said first server is further configured to output, to said at least one application, first information indicating excessive fluctuation in blood glucose level when the standard deviation is greater than a first product of the average and a first factor for visual output of the first information by said at least one application;
wherein said first server is further configured to output, to said at least one application, second information indicating ideal fluctuation in blood glucose level when the standard deviation is smaller than a second product of the average and a second factor which is smaller than the first factor for visual output of the second information by said at least one application; and
wherein said first server is further configured to output, to said at least one application, third information indicating large fluctuation in blood glucose level when the standard deviation is between the first product of the average and the first factor and the second product of the average and the second factor for visual output of the third information by said at least one application.

18. The system according to claim 17, wherein said at least one application is further configured to generate a graphical user interface that visually outputs a plot including a horizontal axis to represent event labels corresponding to the set of the measured blood glucose values, a vertical axis to represent the average and the standard deviation of the set of the measured blood glucose values, an average indicator to indicate a value of the average, and a standard deviation indicator to indicate a value of the standard deviation, wherein at least a portion of the standard deviation indicator is included within the average indicator.

19. A system for monitoring a physiological condition of a user, comprising:
a first apparatus for personal use including a measuring device configured to measure a first physiological parameter of the user, and to generate a first parameter signal indicating a measured first parameter value of the first physiological parameter measured thereby;

a second apparatus for use by medical professionals including a measuring device configured to measure a second physiological parameter of the user, and to generate a second parameter signal indicating a measured second parameter value of the second physiological parameter measured thereby; and a first server communicatively coupled to said first apparatus via a network for receiving the first parameter signal therefrom, and disposed to receive the second parameter signal via the network;

wherein each of the measured first and second parameter values is associated with a disease condition, a health condition, a nutrient intake condition, a fitness condition or an exercise condition of the user;

wherein said second apparatus is further configured to additionally measure the first physiological parameter of the user, and to generate a third parameter signal indicating an additionally measured first parameter value of the first physiological parameter measured thereby, and said first server further receives the third parameter signal from said second apparatus;

wherein said first server is further configured to perform statistical analysis on either of the measured and additionally measured first parameter values measured respectively by said first apparatus and said second apparatus; and wherein the statistical analysis performed by said first server includes:

calculating an average and a standard deviation of the measured or additionally measured first parameter values;

outputting first information indicating excessive fluctuation in blood glucose level when the standard deviation is greater than a first product of the average and a first factor;

outputting second information indicating ideal fluctuation in blood glucose level when the standard deviation is smaller than a second product of the average and a second factor which is smaller than the first factor; and outputting third information indicating large fluctuation in blood glucose level when the standard deviation is between the first product and the second product of the average.

20. The system according to claim 19, further comprising a computer terminal placed in the medical institution, wherein at least one of said first apparatus and said computer terminal is configured to generate a graphical user interface that visually outputs a plot including a horizontal axis to represent event labels corresponding to the measured or additionally measured first parameter values, a vertical axis to represent the average and the standard deviation of the measured or additionally measured first parameter values, an average indicator to indicate a value of the average, and a standard deviation indicator to indicate a value of the standard deviation, wherein at least a portion of the standard deviation indicator is included within the average indicator.

* * * * *